United States Patent [19]

Carter et al.

[11] Patent Number: 4,887,453
[45] Date of Patent: Dec. 19, 1989

[54] METHOD AND SYSTEM FOR ON-LINE CALIBRATION AND VALIDATION OF PROCESS INSTRUMENTATION

[75] Inventors: Hudson R. Carter, Alliance; Eugene T. Upperman, North Canton, both of Ohio

[73] Assignee: The Babcock & Wilcox Company, New Orleans, La.

[21] Appl. No.: 202,090

[22] Filed: Jun. 2, 1988

[51] Int. Cl.⁴ .................................... G01N 27/26
[52] U.S. Cl. .................................... 73/1 R; 204/401
[58] Field of Search ............... 73/1 R, 1 G; 204/400, 204/401, 1 T; 340/620

[56] References Cited

U.S. PATENT DOCUMENTS

| | | | |
|---|---|---|---|
| 2,069,562 | 2/1937 | Schnorf | 204/400 |
| 4,236,988 | 12/1980 | Suzuki et al. | 204/400 |
| 4,384,925 | 5/1983 | Setter et al. | 204/401 |
| 4,495,067 | 1/1985 | Klein et al. | 210/87 |
| 4,668,346 | 5/1987 | Entwistle | 204/401 |
| 4,691,168 | 9/1987 | Dzula | 73/1 R |
| 4,713,618 | 12/1987 | Carlson et al. | 73/1 R |
| 4,784,763 | 11/1988 | Hambleton et al. | 210/90 |

OTHER PUBLICATIONS

Light, Truman S., Temperature Dependence and Measurement of Resistivity of Pure Water, *Anal. Chem.* 56, pp. 1138–1142 (1984).

Hunt, R., Barben, T., Eater, L., Conductivity Measurement of High Purity Water in Power Plants, paper #87-1082, ISA, Anaheim, Calif., Oct. 4"8, 1987.

*Primary Examiner*—Robert R. Raevis
*Attorney, Agent, or Firm*—Vytas R. Matas; Robert J. Edwards

[57] ABSTRACT

A method and system are provided for validating monitoring instruments whereby the validating solution contains other analytes normally present in an industrial liquid. The solution is checked for water purity prior to addition of other analytes and is checked for homogeneity after mixing with analytes.

6 Claims, 1 Drawing Sheet

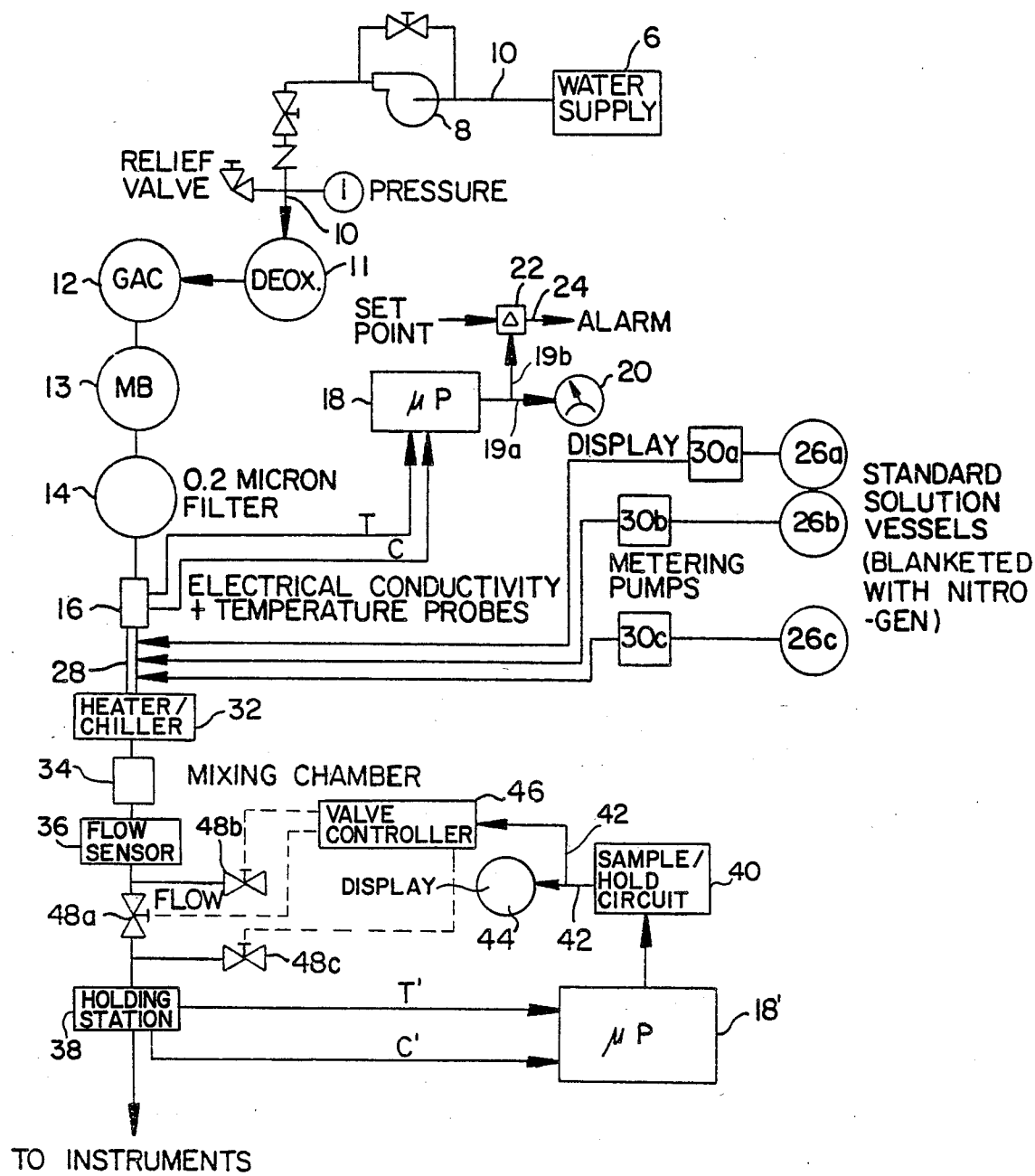

METHOD AND SYSTEM FOR ON-LINE CALIBRATION AND VALIDATION OF PROCESS INSTRUMENTATION

The present invention is directed to a method and system for calibrating and validating the accuracy of on-line monitors of industrial liquids. Such monitors are instruments measuring various chemical contents of the liquids. The method and system is particularly useful for chemical calibration and validation of on-line monitors of aqueous fluids in boiler tubes, superheaters, reheaters, turbines, condensers, and feed water heaters.

For efficient operation and maintenance of an industrial plant, concentrations of various chemicals in aqueous fluids, such as sodium, chloride, sulfate, organic acids, ammonia, hydrazine, silica, dissolved oxygen, dissolved carbon dioxide, bicarbonate, etc. need to be periodically monitored. In the plant, this monitoring is done usually by either continuous or semi-continuous monitoring instruments or by grab sample analytical procedures using a variety of instruments. A particular problem is that each of the instruments must be routinely calibrated according to the instrument vendor procedure and therefore must usually be calibrated on a pure water standard solution containing a single analyte. However, there is no assurance that the instrument, having been calibrated using a pure water standard solution, will be accurate when used to analyze a sample stream usually containing other ion species besides the species being monitored.

A system and method is known for calibrating a plurality of analyte-monitoring devices at any predetermined range of concentration wherein the individual devices are adapted to monitor qualitative and/or quantitative parameters in an aqueous industrial liquid. An example of such a system is described in U.S. patent application Ser. No. 111,241, filed Oct. 21, 1987. The method comprises the steps of preparing a standard sample matrix containing the analytes by mixing deoxygenated, demineralized, purified water free of organic matter with a predetermined volume of each of a plurality of standard analyte solutions, each standard solution consisting essentially of a predetermined concentration of a single analyte in an otherwise deoxygenated, demineralized, purified water, free of organic matter; determining the concentration in the standard matrix sample of each of the added analytes from the amount of each of standard analyte solution added thereto; and introducing portions of the standard matrix solution into each of the analyte-measuring devices for calibration of each of the respective devices.

However, such systems provide no measurement of the purity of the water prior to mixing with the analyte solutions. Also, there are no measurements after the mixing to determine that all transients of temperature and water homogeneity have subsided so that the mixture may properly be used to calibrate and/or validate the monitors.

SUMMARY OF THE INVENTION

The present invention solves the problem of the prior art systems and methods as well as other problems by providing a system which monitors the purity of water prior to mixing with an analyte solution as well as the homogeneity of the mixed solution to determine that all transients have subsided.

To accomplish this, a water conductivity and temperature measurement is taken of the pure water prior to mixing with standard solutions of various chemicals which provide the analyte solution. These temperature and conductivity measurements are inputted to a microprocessor which uses the measurements as variables in the Truman-Light Equation and solves the equation to thereby give the water purity in microsiemens per centimeter. This solved purity level is outputted to a display as well as compared to a predetermined set point of purity and establishes a control signal to activate an alarm when the set point is exceeded.

Similarly the same type of water purity check based on temperature and conductivity is done after the mixing of the pure water with the analyte solution. The microprocessor solves the Truman-Light Equation for water purity making the solution temperature compensated or independent thereof. The water purity is then checked for a stable reading over a predetermined time period to show that transients have subsided.

Thus, on aspect of the present invention is to provide a standardized aqueous solution formed from pure water which is checked for purity.

Another aspect of the present invention is to provide a standardized aqueous solution free of any transients due to mixing of pure water with analyte solutions.

These and other aspects of this invention will be apparent from the following description of the preferred em,embodiment and the claims.

BRIEF DESCRIPTION OF THE DRAWINGS

In the accompanying FIGURE there is shown schematically a system for forming a standardized aqueous matrix for use in calibrating and/or validating industrial chemical monitors.

DESCRIPTION OF THE PREFERRED EMBODIMENTS

Examples of specific analytical tests and/or instruments which are utilized at an industrial site to monitor liquids are those instruments which monitor: specific conductivity, cation conductivity, degassed cation conductivity, dissolved oxygen, dissolved hydrogen, sodium, chloride, phosphate, nitrate, fluoride, pH, silica, corrosion products (iron, copper, zinc, and the like), resin fragments, total organic carbon (TOC), sulfate, ammonia, hydrazine, organic acids, turbidity, and the like. In some instances several of the analytical instruments for testing several of the parameters will be clustered in a single module, which is convenient when some parameters (or analytes) are monitored on-line, and others are monitored by withdrawing samples (grab sampling). The more automated and modularized the monitoring facility, the more difficult and inconvenient it is to calibrate each individual monitoring instrument according to its particular manufacturer's calibration procedures, which usually require a pure water sample containing only the analyte of interest. Thus the present invention provides a system and method which facilitates an essentially simultaneous calibration of all monitoring instruments or at least modules of monitoring instruments without having to produce separate calibration samples for each instrument and being assured that the calibration and/or validation mixture is formed from pure water and has stabilized and is not in any transient state.

Referring to the FIGURE, a schematic is shown of the invention for use in the validation and/or calibration of analytical instruments. A high purity water, such as a condensate 6, is utilized as a starting material for forming the matrix standard solution solution. The condensate is pumped by a pump 8 through a line 10 to a deoxygenator 11, such as $SO_3$-form anion deoxygenation tank, to remove the dissolved oxygen. Then the water is passed into a granular activated charcoal tank (GAC) 12 to remove all organic matter. The water is then demineralized in demineralizer 13, such as a mixed bed $H^+OH^-$ demineralizer (MB), to remove trace ionic impurities. The water is finally purified by filtering through a fine filtration membrane 14 (such as a 0.2 micron filter) to remove suspended material.

To check the purity of the treated water a water conductivity and water temperature measurement is taken at station 16 which has a conductivity probe and a resistance temperature device (RTD) to make these measurements and transmits them along respective lines C and T to a microprocessor 18. The microprocessor is programmed to solve the Truman-Light equation which relates water temperature and conductivity to water purity in microsiemens per centimeter according to the following relationship: (water purity=f(T,C)). Thus the water purity measurement is temperature compensated or independent thereof. The water purity signal is sent by the microprocessor 18 (along line 19(a) to a display 20 and (along line 19(b) to a difference station 22 where it is compared to a set point or predetermined level of water purity which must be maintained. Should this level be exceeded, a control signal along line 24 will actuate an alarm. Thus, water purity is insured prior to mixing with known chemical solutions.

The pure water is then mixed with stock standards stored in stock storage tanks 26a, 26b, and 26c blanketed under an inert atmosphere, such as nitrogen. These chemicals from the tanks are injected into a static mixture tube 28 via respective precalibrated precision metering pumps 30a, 30b, and 30c, respectively. While three storage tanks 26a, 26b and 26c are shown, it is evident that more or fewer tanks may be utilized, depending on the number of stock solutions which are to be utilized. In a preferred embodiment of particular applicability to a power utility, each of the tanks will contain a plurality of stock standardized chemicals. For example tank 26a may contain a mixture of chloride, sulfate, sodium, potassium, carbon dioxide, hydrazine, ammonia, silica, fluoride and phosphate; tank 26d may contain calcium, magnesium, formic acid and propionic acid; and tank 26c may contain air-saturated water. The amount of each of the stock solutions in tanks 26a, 26b, and 26c which are injected into the static mixture tube 28 can be measured by the precalibrated precision metering pumps 30a, 30b, and 30c. The precision metering pumps 30a, 30b and 30c may be micrometer flow adjustable, allowing for injection of chemical species at different concentrations covering instrument operating ranges.

The combination of pure water and injected solution is then sent to a heater/chiller 32 which will either raise or lower the temperature of the mixture to 77° F. ±1° F. as is appropriate depending on summer or winter conditions at the forming of the mixture.

The heater/chiller thus takes the sample temperature to 77° F. which is the calibration temperature of the monitors or instruments verified. Next, the homogeneous standard sample matrix is thoroughly mixed in mix chamber 34 and sent through a flow sensor assembly 36.

From mix chamber 34 measured amounts of the standard matrix solution are conducted to the various instruments or instrument modules to calibrate and/or validate individual devices (not shown).

Prior to being sent to the monitoring instruments (not shown) the standard matrix solution is sent through a station 38 having conductivity probe and an RTD, as in station 16, which measures and sends water temperature and water conductivity signals along lines T' and C', respectively to a microprocessor 18'. The microprocessor 18' is similarly programmed to solve the Truman-Light equation for water purity as was described with respect to microprocessor 18. In fact, the microprocessor 18 may be shared by stations 16 and 38 on a time sharing basis instead of using two microprocessors with the solved outputs being appropriately switched to either the difference station 22 and display 20 or a sample and hold circuit 40 having a built in timer.

The circuit 40 receives the water purity signal, or in the case the water impurity signal, from the microprocessor 18' which is temperature compensated by virtue of the Truman-Light equation. Thus the ±1° F. variations of the heater/chiller 32 are effectively eliminated. The only variation which will occur is then due only to variations in water impurity. Such variations would originate with transients in the mixing of pure water and solutions at pipe 28. Thus the circuit 40 periodically samples the output of microprocessor 18' and compares it with the previous output sampled and held therein. After a predetermined period without any changes, an output signal is produced by the circuit 40 along line 42 indicating that all transients have subsided and the solution is proper for instrument calibration and/or validation.

The output signal 42 is sent to go/no go display 44, which may be a green light/red light display, and to a valve actuator controller 46 which controls valves 48a, 48b, and 48c. Thus valves 48a, 48b, and 48c may be selectively closed or opened to divert fluid flow from the instruments as required.

It should be noted that the alarm signal from line 24 may also be used to actuate the valve actuator controller 46 if required. This would make the valves 48a, 48b, and 48c selectively responsive to water purity in providing validation fluid to the instruments. Also another equation for water purity could be used to program the microprocessors 18 and 18'. One each equation is the Marsh equation which is similarly a function of water temperature and conductivity.

The size of the system shown in the FIGURE may be varied depending upon the chemical species of interest, number of on-line monitors, flow rate of the high purity water system, and the like. The stock solutions which are used for tanks 26a, 26b, and 26c are themselves prepared preferably from deoxygenated, organic free, demineralized filtered water and reagent grade chemical species. Aliquots of stock solutions may be then transferred into the tanks 26a, 26b, and 26c and proper concentrations calculated.

Preparation of the dissolved oxygen stock standard in tank 26c may be obtained by introducing filtered effluent from a high mix bed demineralizer to the reservoir 26c and allowing the water to be air equilibrated at standard temperature and pressure. After equilibration, the water is assayed for dissolved oxygen using standard titrametric procedures.

The validation of dissolved oxygen analyzers (not shown) may be performed separately when carbon dioxide is present in the chemical test matrix since air equilibrated water will contain carbon dioxide. A separate validation for dissolved oxygen is only necessary when carbon dioxide is intentionally added to validate an instrument measuring carbon dioxide.

The present system is advantageous in that it provides for validating acceptable performance of an analytical instrument, multiple instruments of the same type or multiple instruments of different types. It is further advantageous in that it provides the validation of instrument performance at any desired concentration level which may be obtained by adjusting the micrometer on the precalibrated metering pumps 30$a$, 30$b$, and 30$c$ which meter each of the stock solutions into the standard matrix. It is further advantageous in that instrument performance may be validated and can be conducted simultaneously and at various concentration levels on various analytes such as sodium, chloride, hydrazine, ammonia, dissolved oxygen, silica and other analyzers. Thus after calibration of each instrument according to the vendors' procedures, this calibration can be verified so that each analyzer will perform satisfactorily in the presence of the other chemical species present in the industrial liquid. The present invention provides a convenient, semiautomatic means to achieve multi-instrument validation, particular on site, of an industrial liquid.

Certain modifications and improvements will occur to those skilled in the art after considering the present disclosure. It will be understood that all such modifications and improvements have been deleted herein for the sake of conciseness and readability but are properly included with in the scope of the following claims.

We claim:

1. A system for producing a validating solution for a process instrument measuring the analyte content of a water solution, comprising:
    a water supply;
    means for producing pure water fluidly coupled to said water supply, said pure water reproducing means having an outlet for the pure water;
    a temperature measuring device situated in the pure water at the outlet to measure the temperature thereof and establish a signal indicative thereof;
    an electrical conductivity measuring device situated in the pure water at the outlet near said temperature measuring device to measure the conductivity thereof and establish a signal indicative thereof;
    a microprocessor connected to said temperature measuring device and to said conductivity measuring device to receive the signals therefrom, and being programmed to use these signals to solve a water purity equation and establish an output signal indicative thereof;
    means for maintaining water purity responsive to changes in the output signal of said microprocessor; and
    means for adding analytes to the pure water to provide a solution suitable for validating the measuring instrument.

2. A system as set forth in claim 1 wherein said microprocessor is programmed to solve the Truman-Light equation.

3. A system as set forth in claim 1, wherein said microprocessor is programmed to solve the Marsh equation.

4. A system as set forth in claim 1, wherein the means for producing pure water includes:
    means for deoxygenating the water fluidly coupled to said water supply;
    means for removing organic matter from the deoxygenated water fluidly coupled downstream from said deoxygenating means;
    means for removing ionic impurities from the water fluidly coupled downstream from said organic matter removal means; and
    at least one filter for removing particulate material from the water fluidly coupled downstream from said ionic removing means thereby producing pure water.

5. A system for producing a validating solution for a process instrument measuring the analyte content of a water solution, comprising:
    a water supply;
    means for producing pure water fluidly coupled to said water supply, said pure water producing means having an outlet for the pure water;
    a temperature measuring device situated in the pure water at the outlet to measure the temperature thereof and establish a signal indicative thereof;
    an electrical conductivity measuring device situated in the pure water at the outlet near said temperature measuring device to measure the conductivity thereof and establish a signal indicative thereof;
    a microprocessor connected to said temperature measuring device and to said conductivity measuring device to receive the signals therefrom, and being programmed to use these signals to solve a water purity equation and establish a control signal indicative of the water purity of said pure water means prior to producing a validating solution;
    means for maintaining water purity responsive to changes in the control signal of said microprocessor;
    means for adding analytes to the pure water to provide a solution suitable for validating the measuring instrument, said solution being sent to a holding station;
    a second electrical conductivity measuring device situated in the solution at the holding station to measure the electrical conductivity of said solution and establish a signal indicative thereof;
    a second temperature measuring device situated in the solution at the holding station near said electrical conductivity device to measure the temperature of said solution and establish a signal indicative thereof;
    means for receiving the signals of said second electrical conductivity measuring device and said second temperature measuring device from the holding station and calculating water purity therefrom to establish an output signal indicative thereof after producing the validating solution: and
    a sample and hold circuit responsive to the water purity output signal from said receiving and calculating means to establish a control signal indicative of a stabilized solution for instrument validation.

6. A system for producing a validating solution for a process instrument measuring the analyte content of a water solution, comprising:
    a water supply;
    means for deoxygenating the water fluidly coupled to said water supply;
    means for removing organic matter from the deoxygenated water fluidly coupled downstream from said deoxygenating means;

means for removing ionic impurities from the water connected downstream from said organic matter removal means;

at least one filter for removing particulate material from the water connected downstream from said ionic removing means, said at least one filter having an outlet from which pure water flows;

a temperature measuring device situated in the pure water at the outlet to measure the temperature thereof and to establish a signal indicative thereof;

an electrical conductivity measuring device situated in the pure water at the outlet in a position near said temperature measuring device to measure the conductivity of the pure water and establish a signal indicative thereof;

a microprocessor connected to said temperature measuring device and to said conductivity measuring device to use the signals therefrom to calculate water purity as a function of these signals and establish a control signal indicative of the water purity prior to producing a validating solution;

means for maintaining water purity responsive to changes in the control signal of said microprocessor;

means for adding analytes to the pure water or provide a solution suitable for validating the measuring instrument, said solution being sent to a holding station;

a second electrical conductivity measuring device situated in the solution at the holding station to measure the electrical conductivity of said solution and establish a signal indicative thereof;

a second temperature measuring device situated in the solution at the holding station near said electrical conductivity device to measure the temperature of said solution and establish a signal indicative thereof;

means for receiving the signals of said second electrical conductivity measuring device and said second temperature measuring device from the holding station and calculating water purity therefrom to establish an output signal indicative thereof after producing a validating solution; and a sample and hold circuit responsive to the water purity output signal from the receiving and calculating means to establish a control signal indicative of the stabilized solution for instrument validation.

* * * * *